United States Patent [19]

Dimmer

[11] Patent Number: 4,980,124
[45] Date of Patent: Dec. 25, 1990

[54] DENTAL RESTORATION AND METHOD FOR ITS PRODUCTION

[76] Inventor: David C. Dimmer, 2080 E. Baywood Dr., Oregon, Ohio 43618

[21] Appl. No.: 373,333

[22] Filed: Jun. 29, 1989

[51] Int. Cl.⁵ .................................................. G22F 7/00
[52] U.S. Cl. ........................................ 419/9; 433/207; 433/208; 433/223; 433/227; 433/217.1
[58] Field of Search ................... 419/9; 433/207, 208, 433/223, 227, 217.1

[56] References Cited

U.S. PATENT DOCUMENTS

| | | | |
|---|---|---|---|
| 1,172,918 | 2/1916 | Thorp | 433/206 |
| 1,734,676 | 11/1929 | Jaques, Jr. | 433/208 |
| 4,062,676 | 12/1977 | Knosp | 75/165 |
| 4,132,830 | 1/1979 | Tsai | 428/450 |
| 4,181,757 | 1/1980 | Youdelis | 427/229 |
| 4,273,580 | 6/1981 | Shoher et al. | 75/165 |
| 4,459,112 | 7/1984 | Shoher et al. | 433/222.1 |
| 4,492,579 | 1/1985 | Shoher et al. | 433/222.1 |
| 4,698,021 | 10/1987 | Shoher et al. | 433/222.1 |

OTHER PUBLICATIONS

Flexobond System, Exhibit A-1 and Exhibit A-2.
"Renaissance Crown Plus", Williams Dental Co.
Toledo Blade, 2/15/88, "Dimmer's Crown".
Barron's Current Corporate Reports, 12/21/87, p. 47.
Dental Lab Management Today, Nov./Dec., 1987.

*Primary Examiner*—Stephen J. Lechert, Jr.
*Attorney, Agent, or Firm*—Willian Brinks Olds Hofer Gilson & Lione

[57] ABSTRACT

An improvement is provided in the so-called "Foil" system for producing jacketed porcelain dental crowns. One of the most significant improvements is the formation of a crush-resistant coping comprised of a die-conforming noble metal foil and a bonded sintered alloy. Extremely strong crowns are produced in a short order of time by applying the porcelain over such a coping.

19 Claims, No Drawings

DENTAL RESTORATION AND METHOD FOR ITS PRODUCTION

TECHNICAL FIELD

This invention relates to the field of dental restoration and more particularly to porcelain crown restorations. Even yet more specifically, the invention relates to a method for forming a porcelain veneer crown or a reinforced porcelian jacket crown.

BACKGROUND ART

Dental porcelain, a material composed of feldspar, quartz and kaolin, is commonly used in fabricating dental restorations. Full porcelain crowns, or restorations, although aesthetically highly desirable have generally been employed in the past only for coverage of anterior teeth, where aesthetics is the prime consideration. The reason for this is because porcelain is inherently a structurally weak material. One technique for making a porcelain crown involves the use of a malleable foil which is ultimately removed from within the fused porcelain.

Because of this deficiency with full porcelain restorations, a porcelain veneer cast metal crown has been extensively employed. This crown has a relatively thick noble metal substructure formed from casting an investment of a wax or plastic pattern of the prepared tooth. Dental porcelain is then applied in layers over part, or all, of the substructure and fired at high temperatures to form the veneer. Since the thickness of the substructure is substantial, material costs in such a cast metal crown are high due to the use of large amounts of expensive noble metals. These type crowns are not totally acceptable either because the thickness of the metal substructure minimizes the permissible thickness which may be employed for the porcelain veneer. Of course, any exposure of the metal substructure will detract from the aesthetics of the restoration. This can result, for example, if the porcelain veneer were to be chipped or if the porcelain veneer were too thin as might be the case if the cast metal substructure is too thick. Finally it will be appreciated that the manufacture of such a restoration, with the waxing, casting and machining that is required, is very expensive because of its being labor intensive.

In an attempt to address some of the above deficiencies, so-called "foil" systems have been developed to produce a reinforced porcelain jacket crown restoration. Unfortunately, the crowns produced by such techniques are also structurally weak and fragile Furthermore, during an intermediate phase of this production technique a weak and malleable structure is produced which is easily crushed, even accidentally. This results in substantial amounts of wasted time and materials which consequently has an adverse impact on production economics.

Briefly, the "foil" technology involves the use of a deformable or malleable noble metal foil which is conformed to the shape of the die of the prepared tooth. A bonding agent may be employed on the outer surface of the conformed foil and then porcelain is applied over such an understructure. The conforming foil is very easily deformed and great care must be exercised in its utilization, especially during the application of the porcelain. Furthermore, because of this deformability and inherent weakness in the substructure, the final crown likewise is subject to deficiencies because of its poor strength. Additionally such "foil" technology is not adaptable to forming dental bridge restorations.

U.S. Pat. Nos. 4,459,112 and 4,273,580 exemplify "foil" systems. It will be readily apparent from the teachings of these patents that the copings which are formed have virtually no crush-resistance whatsoever. The technique disclosed in U.S. Pat. No. 4,459,112 is likewise labor intensive because of the care which must be exercised in forming the pleated, or umbrella-like, structure and also, in following the preferred embodiment, in forming small slotted openings through portions of the foil.

Thus from the foregoing, it will be seen that there is a need in the art to provide for an improved crown which can be manufactured by an economical process. In order to be economical there is a need that this process eliminate previously required steps including eliminating the need for waxing, casting and machining of a substructure. There is also a need in the art that the method not require the use of thick substructures to thereby increase the economics of the system by greatly minimizing the amount of noble metal which need be employed. Additionally, in contrast to the "foil" systems which produce an easily crushed coping, or substructure, there is a need in the art to provide for a process wherein the coping is crush-resistant. In that way the coping can be more easily handled during crown manufacture and, ultimately results in the formation of a stronger, more durable final dental restoration. Such strength would also allow the process to be adapted to forming a bridge. Additionally, there is a need in the art to provide for a process which does not require the additional step of slitting portions of a "foil".

BRIEF DESCRIPTION OF THE INVENTION

In accordance with the present invention the foregoing needs in the art are satisfied.

In accordance with the present invention those needs are satisfied by providing a dentail restoration comprising: (A) a composite coping of (i) an inner foil conforming to a die of a prepared tooth and (ii) a substantially uniform alloy coating externally disposed on said foil in an amount sufficient to provide a crush-resistant unitary coping of composite construction; and (B) a porcelain veneering material on said composite coping When the unfired porcelain veneering material is fired and fused it tenaciously bonds to the alloy coating of the crush-resistant unitary substructure and provides for strong dental restoration. The method aspect of this invention for forming such a dental restoration comprises:

(i) conforming a dentally acceptable, malleable foil to the shape of a die of the prepared tooth (ii) applying effective, inchoate, crust-resistant improving amounts of a dentally acceptable particulate alloy coating unto the external surface of said conforming foil (iii) heating said coated foil for a time and at a temperature sufficient to sinter said coating and foil into a crush-resistant, unitary coping, said coating being substantially uniform (iv) coating a veneering material over said coping.

The terminology effective, inchoate, crush-resistant improving amounts of alloy, as will be readily apparent, means, first of all, that when the alloy is initially applied it is not effective to provide crush-resistance but it is applied in sufficient quantities so that when it is finally heated, such as to sinter the alloy, there will be sufficient alloy present to provide a crush-resistant substructure, i.e. a coping or thimble which is crush-resistant. As used herein the term crush-resistant refers to the ability of the present copings, or thimbles, to resist being crushed when strongly compressed between the index finger, or any other finger for that matter, and the thumb. The copings or thimbles formed by the prior art "foil" systems completely lack such crush-resistance.

In the usual technique the die will be removed once the malleable foil has been made to conform to it, and the internal portion of the conformed foil is then filled with a shape retaining material, preferably a refractory material, into which is inserted a suitable stem to allow convenient handling. Particulate alloy, preferably in paste form is then uniformly applied in one or more steps, dried and sintered. The shape retaining material is removed after the heating step and leaves behind the crush-resistant coping which is ready to receive an application of the veneering material. At this stage, the present coping, because of its crush-resistance can be easily coated with the appropriate dental porcelain and there will be no fear of crushing or distorting this substructure. It will be understood when reference is made to forming a veneer, or a porcelain veneer, or applying porcelain, that conventional techniques are contemplated and such terminology comprehends within its scope the typical initial opaquing step.

Because of the present unique method, it is possible to build a radially extending ledge on the coping surface when applying the high strength particulate alloy coating. In this way, once fired to produce the crushed-resistant coping, a ledge will then exist to provide additional structural support for the finally applied porcelain. The process of this invention is thus uniquely adapted to forming a metal finish line.

Another advantage of the present invention, compared to making crowns by more recent "foil" techniques, is that the initial coating of the porcelain in step (iv), that is after the usual op quing, can be done over the entire height of the coping. Opaquing, of course, refers to the application of a masking porcelain to the areas to receive porcelain. In the foil technique, as is well known, the porcelain must first only be applied over a portion of surface and fired and then it can be applied over the remaining part of the surface; this double step is necessary in order to prevent warpage due to the propensity of the porcelain to shrink Thus from the foregoing those skilled in the art will readily appreciate that a problem has been solved in the art and a need satisfied. This technique eliminates the need for waxing, casting and machining. It likewise allows the use of smaller quantities of noble metals, thereby being economical from a raw material point of view. The present process is not labor intensive and it provides an improvement over the other "foil" techniques by providing for a substructure, or coping, or thimble, which has sufficient crush-resistance so as to withstand the needed handling and thereby preclude the destruction of any of the preform understructures or copings, during, for example, the application of porcelain. The process can also be used to form crowns during the process of making a bridge.

DETAILED DESCRIPTION OF THE INVENTION INCLUDING THE BEST MODE OF CARRYING IT OUT

The first step in preparing a dental restoration in accordance with the present invention, be it a crown per se or an abutment crown for forming a bridge, is the preparation of a die(s) of the prepared tooth, namely the one which are to be restored. The die is generally referred to, in the art, as either a stone, epoxy or a silver die. This step is done in a known manner and generally along the same lines as that practiced with any of the current "foil" systems. Next a dentally acceptable malleable foil, that is, a foldable foil which is acceptable by dental standards is applied to the die and conformed to the shape of the die. The conforming step generally would involve folding and trimming of the foil followed by any suitable swagging type operation, including hammering, compression, as by the application of pressure to the foil by hand or with the use of various utensils and/or various types of pressing, including isostatic pressing. The foil itself will desirably be a noble, or precious metal, or a noble metal based alloy. Representative noble metals include gold, silver, platinum, palladium, iridium and rhodium. As will be apparent three features are generally important in the selection of the foil. First of all, the foil must be dentally acceptable. Secondly, the foil must be malleable, or foldable, and finally the foil, in conjunction with the subsequently applied alloy, must produce the crush-resistant coping. Crush-resistant, as previously noted, means that the coping cannot be crushed between the thumb and any of the fingers. Representative of compositions for suitable foils are those made of gold-palladium alloys, gold - platinum alloys, platinum and most preferably a foil which is substantially completely palladium. Laminated structures of suitable foils may also be employed and an especially preferred laminated construction for the foil is a laminate of gold and palladium. Outstanding results with the gold-palladium foil laminate have been obtained by disposing the gold layer toward the die. For example, a laminate formed from a 24 karat gold foil and a palladium foil can be easily manufactured by simply compressing the two foils together to form a laminate. The thickness of the foil which is employed desirably will vary between about 0.001 to about 0.0015 inches. Foils which are suitable for this purpose, for example the palladium foil, may be obtained from a variety of dental and jewelry supply companies and it is preferred to use a thickness of about 0.0015 inch. Generally palladium foils with a thickness in excess of about 0.002 or 0.003 inch are not sufficiently malleable for expediently conforming it to the die. The above indicated gold - palladium laminated foil can be produced from a 24 karat gold foil having a thickness of about 0.0015 and the above indicated palladium foil having a thickness of 0.0015 inch. The foil is cut such that when disposed circumferentially around the die it is of sufficient axial length, or height, to more than cover all mesial, distal, labial and lingual surfaces; it is also of sufficient height to ensure that it is capable of covering all incisal and occlusal surfaces The material, or foil, preferably is generally, first of all, wrapped around the prepared die, the ends brought together, crimped into a seam and then folded back against the circumference of the tooth. The upper portions are then pinched together and folded back over the incisal and/or occlusal surfaces of the tooth. Excess material can, of course, be cut away in any convenient manner: The folding of the foil can be done substantially identical to that done currently in producing or making Flexobond System crowns or other existing methods used to make porcelain jackets. The application, folding and conforming of the foil to the die may generally be done also as contemplated in U.S. Pats. Nos. 4,273,580 and 4,459,112. There is no need to use slitted foils, however, in the present invention. The foil folding can also be done, for example, in the manner done in the past for making porcelain jackets for anterior teeth. In the preferred technique, a palladium foil and the above indicated laminated foil of gold and palladium were employed. The respective foils were conformed to the shape of the die by first manually conforming them as with the hand and small utensils like tweezers and then by employing isostatic pressing. That is, the die with the hand conformed foil upon it was placed in a swagger or press, in the nature of a piston and cylinder with the cylinder containing a molding compound such as modeling clay. Such a swagger or press are those commonly used in making porcelain crowns or in making reinforced jackets using foil systems.

Upon completing the step whereby the dentally acceptable malleable foil is conformed to the shape of the die the foil usually is trimmed or cut down to the margin, that is to the cut upper portion of the tooth to be restored or where the metal will meet the end of the tooth.

At this point preferably the die is removed from the conforming foil. This can simply be done by inserting the foil into a soft red boxing wax and then withdrawing the die therefrom. The conformed foil is generally then heat cleaned by placing it over a Bunsen burner. It is believed that this is a temperature of about 2000° F. and times on the order of 15 seconds have produced highly desirable results. In the case of the gold-palladium laminate foil it appears that the gold foil alloys with the palladium foil and it is preferred to allow sufficient time to allow the gold to flow during this heating. This results in a welding or bonding of the palladium seams with the gold and, apparently, an increase in the strength of the foil.

Next steps are taken to allow for the more convenient and easily handling of the conformed foil. In this phase of the process the internal cavity of the conformed foil is generally filled with a shape-retaining material, preferably a refractory, i.e. high temperature resistant material. The purpose of the shape-retaining material, obviously, is to maintain the shape of the conformed crushable foil until a crush-resistant coping is formed. This refractory material can be any suitable material which can be hardened or solidified, can withstand the subsequent processing temperatures and can be subsequently easily removed. Such materials commercially available and preferred materials include the self-hardenable system available under the designation SINTERLOY Refractory Die Material (Denpac Corp.) and VHT casting investment material (Whipmix Corp.) and PLACIT soldering investment. The latter material is desirably used for crowns and can be used for bridges as can the former two. The first two are two part self-hardenable systems and the latter is a single part self-hardening system available from American Dental Supply of Easton, Pa. under the designation PLACE-IT 2. The hardening rate can, of course, be increased by heating as, for example, with a hair dryer. After filling the cavity, and prior to drying or solidifying the refractory material, a suitable small pin is inserted into the refractory to provide a stem for easy handling. Suitable are the ceramic rods or pins available from Denpac Corp. Once the refractory material is applied and the stem inserted, the shape-retaining material is allowed to solidify. In order to provide better bonding for the subsequently applied alloy, the externally disposed surface is then grit blasted, for example, with a white aluminous oxide available from dental supply houses. This also appears to strengthen the foil.

The die which now internally carries the stem and a solidified shape-retaining amount of the shape-retaining refractory material is now ready to receive crush-resistant improving amounts of a dentally acceptable particulate alloy coating on its external surface. That is, there is now applied to the external surface a sufficient amount of a dentally acceptable particulate alloy coating so that upon being sintered it becomes strongly bonded to the external surface of the conforming foil, and the foil and the sintered alloy interact, resulting in the formation of a highly desirable crush-resistant unitary coping. It is generally preferred that care be exercised in applying the particulate alloy, so that upon subsequent sintering by heating a substantially uniform coating is obtained. That is, it is desired to form a coating which generally covers the entire surface in a uniform manner and not a coating which is characterized by isolated globules.

Suitable particulate alloy formulations which will result, along with the foil, in a unitary coping which cannot be crushed by the application force between the thumb and any of the fingers, will be routinely and easily selected by those skilled in the art. Desirably they are palladium based compositions. A particularly preferred material is the halide free material commercially available under the designation Sinterloy alloy material from the Denpac Corporation. Particularly preferred compositions contain about 70 to 80% by weight palladium and include copper, gallium, optionally gold, ruthenium and indium. Thus, particularly suitable compositions include about 78 to 80% by weight palladium, 0–6% by weight gold, about 8 to 10% by weight copper, about 9 to 9.5% by weight gallium and up to about 1% by weight ruthenium. Suitable SINTERLOY alloys are reported to have melting ranges of, for example, about 2145° F. to about 2210° F.

The particulate alloy, for example, a Sinterloy alloy material, is desirably applied as a paste form in a suitable volatile or pyrolizable carrier system. The alloy's carrier system may be a resin binder with a vaporizable liquid. The function of the carrier system is to provide some strength and integrity to the applied alloy layer until final fusing or sintering when the system is volatilized or pyrolyzed. Two especially suitable paste form alloy materials are the palladium based alloys available from Denpac under their designation 80NS PLUS and 75 PLUS, the former is believed to contain about 2% Au and the latter about 6% Au. These alloys are especially conveniently sintered to their final form using a Denpac Sinterloy Processor with programmed vacuum heating from about 250° C. to about 1140° C. for about 10 minutes followed by final sintering. The time and temperature used to finally sinter the alloy should be such that no significant distortion of the underlying foil occurs. For example, a temperature of about 1144° F. for about 12 minutes causes undesirable distortion with the 6% Au material.

Suitable alloys may be applied in a single step by, for example, brushing, or the material can be gradually buitl up in a series of steps with intermediate drying cycles or, if deired, even a sintering or fusing intermediate step. The material is finally fused or sintered usually between about 1100° to 1200° C. Typical thicknesses of the finally sintered material preferably will be on the order of about 0.1 mm to about 0.75 mm.

Since the alloy is preferalby applied in the form of a paste, that is, an alloy dispersed in a carrier, it is easy to build up a radially extending ledge portion, of the alloy on the surface of the conforming foil. The ledge can, of course, be a lingual, labial, mesial, distal or buccal ledge or all the mentioned surfaces. This ledge thereby provides additional support for the ultimate veneer or porcelain layer to be applied. When such a ledge is to be provided it is generally preferred to form it in a stepwise manner. That is, it is preferred to apply a slightly greater amount of the alloy paste at the desired location followed by its drying and repeating the steps until teh desired ledge thickness is formed. If the carrier in teh alloy paste is sufficiently volatile, all that needs to be done in between successive applications of the paste is to allow such volatilization or drying. For example, when teh above Sinterloy paste materials are employed all that is required is to allow the applied paste to dry for about 3 to about 15 minutes at a temperature between about 60° C. to about 90° C. in between successive coating applications. Such material has sufficient integrity that sintering is not necessary in between each application step.

After the desired amount of the particulate alloy coating has been applied, the foil and alloy are then heated at a temperature and for a time sufficient to sinter the coating to the foil and form a crush-resistant unitary coping. As indicated the amount of alloy applied should be such that a substantially uniform coating is obtained. Good results have been obtained by heating the foil and coating to form the crush-resistant unitary coping using a Sinterloy Processor available from the Denpac Corporation. Suitable heating cycles using the Sinterloy palladium based alloy have generally been temperatures on the order of about 250° C. to about 1200° C. for about 3 to about 12 minutes. In general it is preferred to apply the alloy in two coats and to effect final sintering at a temperature of about 1140° C. for about 8 minutes. Time and temperature for sintering will, of course, vary but should be sufficient to provide an alloy coating with good cohesive strength to thereby provide the crush-resistant coping.

Because the refractory material which is inserted into the foil prior to forming the crush-resistant coping will not be adherent to the internal surface of the foil, the shape retaining material, after the sintering operation, is simply removed by pulling on the stem, thereby leaving the crush-resistant unitary coping clean and ready to be placed on the die for the application of a porcelain veneer.

Conventional veneering, or porcelain, materials are coated onto the crush-resistant coping using well known technology and procedures. In passing, however, one advantageous feature should be noted. With the present invention the initial application of the veneering material, that is, after the standard opaquing procedure is completed, can be done over the entire height of the coping, that is, down to the margin. This is in marked contrast to the present commercial foil techniques wherein in the initial step the porcelain cannot be applied to the margin. That is, in such prior technique in the first step the porcelain must be applied short of the margin and then margin; otherwise warpage and shrinkage result which distorts the fit of the metal substructure.

Crowns were made in the manner discussed above using the preferred techniques. First of all, the unitary copings were extremely crush-resistant. Secondly, the final crowns were extremely strong when the porcelain was applied and, perhaps the greatest advantage of all with regard to this technique, is that it was done in a very short order of time with very little labor utilization.

The abutment coping, or abutment copings, are made as described earlier in this application. Pontics or dummy substructures are selected from precast, sintered or stamped materials, or waxed and cast to fit the space to be filled. The pontics or dummies are luted with wax or acrylic to make a one piece bridge on the master model. It is then removed and placed in a refractory shape retaining material. When the investment sets or cures the bridge is cleaned and then can be welded or sintered together creating a solid strong one piece metal sub frame which can then be prepared for porcelain in a known manner.

While the above describes the present invention it will, of course, be apparent that modifications are possible which pursuant to the patent statutes and laws do not depart from the spirit and scope of the following claims.

I claim:

1. A method for forming a dental restoration for a prepared tooth comprising:
   (i) conforming a dentally acceptable, malleable foil to the shape of a die of the prepared tooth
   (ii) applying effective, inchoate crush-resistant improving amounts of a dentally acceptable particulate alloy coating unto the external surface of said conforming foil
   (iii) heating said coated foil for a time and at a temperature sufficient to sinter said coating and foil into a crush-resistant, unitary coping, said coating being substantially uniform.

2. The method of claim 1 and further including (iv) coating a veneering material over said coping.

3. The method of claim 2 wherein said foil is a palladium foil

4. The method of claim 3 wherein said alloy is a palladium based alloy.

5. The method of claim 2 wherein said step (i) further comprises: removing said die from said conforming foil; and providing the internal portion of said foil with a shape retaining amount of a shape retaining refractory material.

6. The method of claim 2 wherein said sintered coating has a thickness of about 0.1mm to about 0.75mm.

7. The method of claim 5 and further comprising removing said shape retaining material after step (iii) and prior to step (iv).

8. The method of claim 2 wherein said die includes a surface portion which is free of a radially extending ledge for supporting said veneering material and wherein step (ii) includes building a radially extending ledge on said surface with said alloy.

9. The method of claim 8 wherein said ledge is a lingual ledge.

10. The method of claim 8 wherein said ledge is a mesial ledge.

11. The method of claim 8 wherein said ledge is a distal ledge.

12. The method of claim 8 wherein said ledge is a buccal ledge.

13. The method of claim 2 wherein in step (iv), the initial coating of such material is applied over the entire height of said coping.

14. The method of claim 13 wherein said alloy is about 78-80% by weight Pd and includes copper and gallium and optionally include one or more of gold, ruthenium and indium.

15. The method of claim 13 wherein said alloy has a melting range of about 2145° F. to about 2210° F. and includes about 2%-6% Au.

16. The method of claim 2 wherein said foil is a laminate of a gold layer bonded to a palladium layer.

17. The method of claim 1 wherein said foil is free of slits.

18. The method of claim 1 wherein said alloy is applied on substantially the entire external surface of said conforming foil.

19. The method of claim 17 wherein teh alloyws of step (ii) are applied in a series of steps.

* * * * *